United States Patent [19]
Ohtani et al.

[11] Patent Number: 5,981,778
[45] Date of Patent: Nov. 9, 1999

[54] PROCESS OF PRODUCING ETHER-TYPE THIO-PHOSPHOLIPIDS

[75] Inventors: Mitsuaki Ohtani, Nara; Masahiro Fuji, Higashiosaka, both of Japan

[73] Assignee: Shionogi & Co., Ltd., Japan

[21] Appl. No.: 09/045,924

[22] Filed: Mar. 23, 1998

Related U.S. Application Data

[62] Division of application No. 08/847,771, Apr. 23, 1997, Pat. No. 5,760,270, which is a division of application No. 08/530,763, Sep. 19, 1995, Pat. No. 5,663,405.

[51] Int. Cl.$^6$ ...................... C07C 327/28; C07C 323/16; C09B 11/04
[52] U.S. Cl. ........................ 552/104; 558/248; 558/252; 568/44; 568/45
[58] Field of Search ............................ 549/416; 552/104, 552/105; 556/429; 558/248, 252; 568/44, 55, 45

[56] References Cited

U.S. PATENT DOCUMENTS

| | | |
|---|---|---|
| 5,221,696 | 6/1993 | Ke et al. |
| 5,464,754 | 11/1995 | Dennis et al. ............................ 435/18 |

FOREIGN PATENT DOCUMENTS

| | | |
|---|---|---|
| 4-023999 | 12/1992 | Japan. |
| WO93/09787 | 5/1993 | WIPO. |
| WO95/05479 | 2/1995 | WIPO. |
| WO95/32984 | 12/1995 | WIPO. |

OTHER PUBLICATIONS

Maramatsu, Toshio "Synthesis of Thioether and Thioether Phospholipids" INSERM Symposium No. 23, 1983, 37–40.
Database Beilstein on STN®, Beilstein Informationssysteme GmbH, (Frankfurt, Germany), Beilstein Registry No. 4815230, 1994.
Chemical Abstracts, vol. 121, No. 15, Abstract No. 180120 (abstract of JP–A–94 116 279 (1994).
Chemical Abstracts, vol. 101, No. 11, Absract No. 090651.
S.K. Bhatia et al., *Tetrahedron Lett.*, 28(16), 1729–1732 (1987).
L.J. Reynolds et al., *Anal. Biochem.* 217(1), 25–32 (1994).
M. Murata et al., *Chem. Pharm. Bull.*, 39(5), 1335–1336 (1991).
M. Murata et al., *Chem. Pharm. Bull.*, 40(10), 2849–2851 (1992).
Stewart et al., *J. Lipid Mediators* 4(3), 299–308 (1991).
Bhatia et al., *Synthesis*, 1, 16–20 (1989).

*Primary Examiner*—Michael G. Ambrose
*Attorney, Agent, or Firm*—Wenderoth, Lind & Ponack, L.L.P.

[57] ABSTRACT

A method of producing an ether-type thio-phospholipid of the formula (I):

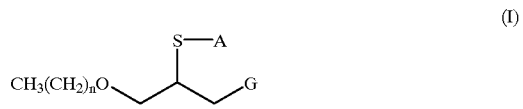

wherein:

n is an integer of 13 to 17;
A is $C_{14}$–$C_{20}$ acyl group;
G is a group selected from the group consisting of:

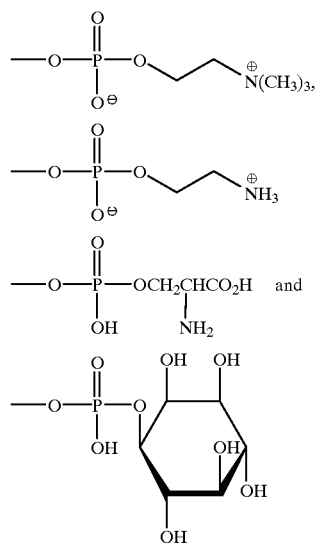

which is useful as synthetic substrate of cytosolic phospholipase $A_2$ inhibitors, said method being applicable to mass production of the compound (I), intermediates therefor and the preparation of the same are provided.

4 Claims, No Drawings

PROCESS OF PRODUCING ETHER-TYPE THIO-PHOSPHOLIPIDS

This is a divisional application of Ser. No. 08/847,771, filed Apr. 23, 1997, now U.S. Pat. No. 5,760,270, which is a divisional of Ser. No. 08/530,763, filed Sep. 19, 1995, now U.S. Pat. No. 5,663,405.

FIELD OF THE INVENTION

This invention relates to novel method of producing synthetic ether-type thio-phospholipid compounds useful as a substrate for cytosolic phospholipase $A_2$, said method being applicable to mass production of compounds (I), intermediates useful therefor and the preparation of the intermediates.

BACKGROUND OF THE INVENTION

Cytosolic phospholipase $A_2$ (cPLA$_2$) is an arachidonic acid-specific enzyme which is of considerable interest due to its potential roles in arachidonic acid release, eicosanoid production and signal transduction. Because of these potential role, there was interest in developing pharmaceutically effective inhibitors of cPLA$_2$, said inhibitors being expected to be useful as, for example, anti-inflammatory agents. In this connection, there has been provided a non-radiometric, spectrophotometric assay for cPLA$_2$ which utilizes synthetic thio-phospholipids as a substrate (Analytical Biochemistry, 217, 25–32, 1994).

As one of candidates, there is an ether-type thio-phospholipid with a wide range of physiological activities, e.g., platelet-activating factor (PAF) (1-alkyl-2-acetyl-2-deoxy-sn-glycero-3-phosphocholine) which is known as a phospho lipid mediator.

Recently, analogues of PAF which can serve as a substrate of PLA$_2$ have been provided. For example, Tetrahedron Lett., 28, 1729 (1987) disclosed thio-PAF (1-O-hexadecyl-2-thioacetyl-2-deoxy-sn-glycero-3-phosphocholine), a derivative of PAF having 2-thioacetyl in place of 2-acetyl group. Various compounds usable as substrates and the production thereof were also disclosed in Japanese Patent Appln. Laid-open Publication No. 116279/1994. However, according to methods which have been known in the art including those described in the literatures above, the intended ether-type thio-phospholipids, especially those having thio-arachidonoyl group in sn-2 position of PAF, could not be prepared in high yield and purity. Thus, the existing methods were not efficient enough to apply to mass production of desired compounds.

Therefore, it has been demanded the development of novel method of producing ether-type thio-phospholipids, which method is applicable to mass production.

SUMMARY OF THE INVENTION

The present invention provides a method of producing ether-type thio-phospholipids which are useful as substrate in the analysis of PLA$_2$ activity.

The present invention also provides intermediates useful for the production of ether-type thio-phospholipids according to the method of the present invention and the process of producing the intermediates.

The method of the present invention has been established as the result of the finding that a certain protocol and intermediates are extremely profitable for carrying out a series of reactions.

Thus, in the course of intensive research for developing industrially-applicable process of producing ether-type thio-phospholipids, the present inventors have found that one of problems of conventional methods results from the fact that the chemically unstable structure of arachidonic acid thioester is generally formed in the midway of total process, which lowers both the purity and yield of the intended compound. After making a great effort, the present inventors have succeeded in solving the problem by devising a procedure consisting of a series of reactions where the thioester structure is formed at the final stage thereby yielding the desired product efficiently.

Specifically, the present invention provides a method of producing a compound of the formula (I)

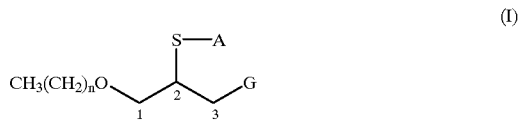

wherein:
n is an integer of 13 to 17;
A is $C_{14}$–$C_{20}$ acyl group;
G is a group selected from the group consisting of:

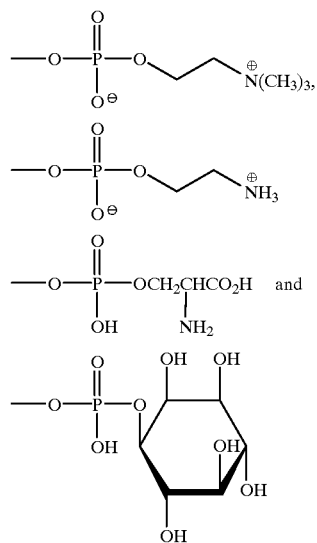

and the stereochemistry in the 2-position is of non-restrictive, which method affords highly pure compound (I) in high yield and is applicable to mass production of the same.

The present method can be illustrated in general by the reaction scheme below:

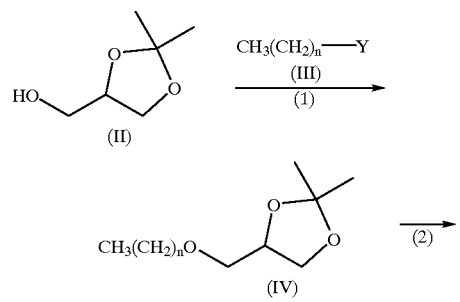

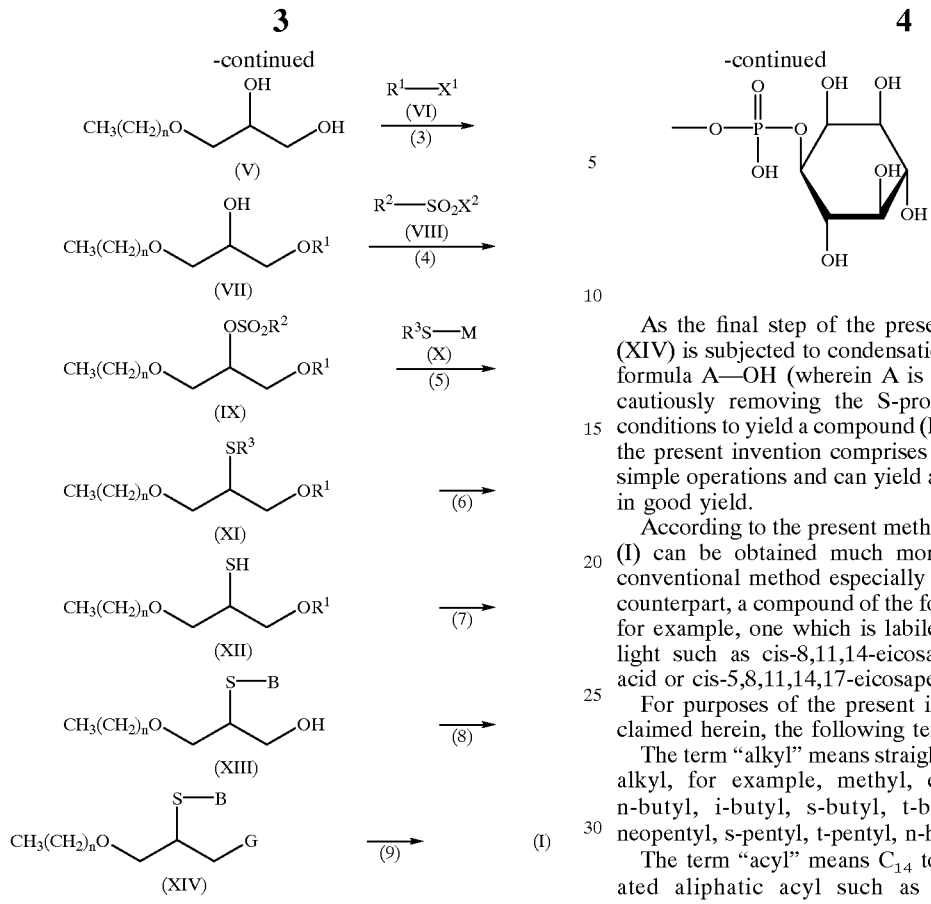

wherein:

n is an integer of 13 to 17;

Y is halogen, alkylsulfonyloxy or arylsulfonyloxy;

$R^1$ is a hydroxy-protecting group;

$X^1$ is halogen;

$R^2$ is methyl, phenyl or p-tolyl;

$X^2$ is halogen;

$R^3$ is alkanoyl or arylcarbonyl;

M is alkali metal;

B is an S-protecting group;

G is a group selected from the group consisting of:

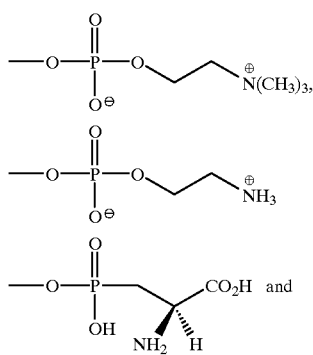

As the final step of the present method, the compound (XIV) is subjected to condensation with a compound of the formula A—OH (wherein A is $C_{14}$–$C_{20}$ acyl group) after cautiously removing the S-protecting group under mild conditions to yield a compound (I) efficiently. The method of the present invention comprises many steps each requiring simple operations and can yield a highly pure compound (I) in good yield.

According to the present method, the intended compound (I) can be obtained much more efficiently compared to conventional method especially when using, as a coupling counterpart, a compound of the formula A—OH of any type, for example, one which is labile to acid, alkali, air and/or light such as cis-8,11,14-eicosatrienoic acid, arachidonic acid or cis-5,8,11,14,17-eicosapentaenoic acid.

For purposes of the present invention, as disclosed and claimed herein, the following terms are defined below.

The term "alkyl" means straight or branched chain $C_1$–$C_8$ alkyl, for example, methyl, ethyl, n-propyl, i-propyl, n-butyl, i-butyl, s-butyl, t-butyl, n-pentyl, i-pentyl, neopentyl, s-pentyl, t-pentyl, n-hexyl, n-heptyl, n-octyl.

The term "acyl" means $C_{14}$ to $C_{20}$ saturated or unsaturated aliphatic acyl such as myristoyl, myristoleoyl, pentadecanoyl, palmitoyl, palmitoleoyl, heptadecanoyl, stearoyl, linoleoyl, nonadecanoyl, eicosanoyl, cis-11-eicosenoyl, cis-8,11,14-eicosatrienoyl, arachidonoyl, and the like, preferably unsaturated acyl, especially arachidonoyl.

The term "halogen" means fluorine, chlorine, bromine and iodine.

The term "aryl" means phenyl, P-tolyl, 2,4,6-trimethylphenyl, naphthyl.

The term "alkyl- or aryl-sulfonyloxy" means a group formed by substituting a sulfonyloxy group with an alkyl or aryl group(s) as defined above.

The term "arylcarbonyl" means a group formed by substituting a carbonyl group with an aryl group(s) as defined above.

The term "alkanoyl" means $C_1$ to $C_8$ alkanoyl such as acetyl, propionyl, butyryl, pentanoyl, hexanoyl, heptanoyl, octanoyl.

The term "alkali metal" means lithium, sodium and potassium.

S-protecting groups usable in the present method can be selected from those conventionally used in the art, for example, t-butoxycarbonyl, benzyloxycarbonyl, benzyl, 4-methoxybenzyl, 3,4-dimethoxybenzyl, 4-nitrobenzyl, diphenylmethyl, trityl, acetyl, benzoyl and the like.

Hydroxy-protecting groups usable in the present method are essentially the same as S-protecting group as well as trimethylsilyl, dimethyl-t-butylsilyl, diphenyl-t-butylsilyl, methoxymethyl, tetrahydropyran-2-yl and the like.

DETAILED DESCRIPTION OF THE INVENTION

The starting material of the present method, i.e., 1,2-O-isopropylidene-glycerol (II), can be prepared in a conventional manner or is available from commercial source.

The compound (II) is reacted with a compound of the formula (III):

  (III)

wherein n is an integer of 13 to 17, Y is halogen, alkylsulfonyloxy or arylsulfonyloxy in the presence of a base to give a compound of the formula (IV):

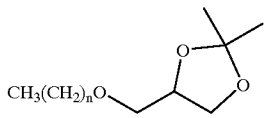  (IV)

wherein n is an integer of 13 to 17.

The compound (IV) is then hydrolyzed with an acid to give a compound of the formula (V):

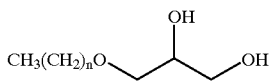  (V)

wherein n is an integer of 13 to 17.

The compound (V) is reacted with a compound of the formula (VI):

  (VI)

wherein $R^1$ is a hydroxy-protecting group and $X^1$ is halogen in the presence of a base to give a compound of the formula (VII):

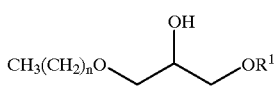  (VII)

wherein n and $R^1$ are as defined above.

The compound (VII) is reacted with a compound of the formula (VIII):

  (VIII)

wherein $R^2$ is methyl, phenyl or p-tolyl and $X^2$ is halogen to give a compound of the formula (IX):

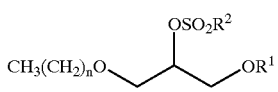  (IX)

wherein n, $R^1$ and $R^2$ are as defined above.

Compound (IX) is reacted with a compound of the formula (X):

  (X)

wherein $R^3$ is alkanoyl or arylcarbonyl and M is an alkali metal to give a compound of the formula (XI):

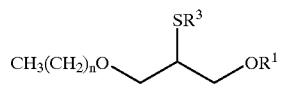  (XI)

wherein n, $R^1$ and $R^3$ are as defined above.

The compound (XI) is then converted, by removing $R^3$, into a compound of the formula (XII):

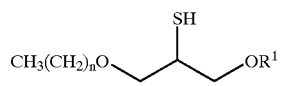  (XII)

wherein n and $R^1$ are as defined above.

The compound (XII) is subjected first to protection of thiol group and second to removal of $R^1$ or vice versa to give a compound of the formula (XIII):

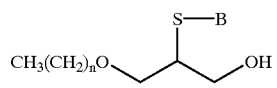  (XIII)

wherein B is an S-protecting group and n is as defined above. An embodiment where $R^1$ of compound (XII) is trityl group is preferable because the compound (XIII) can be obtained in one step by means of trityl-transfer reaction wherein the group is converted into S-protecting group.

The compound (XIII) is subjected to 1) the reaction with a compound of the formula:

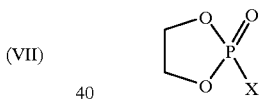

wherein X is halogen to form a cyclic phosphoric ester bond in its primary hydroxyl group and then with trimethylamine or ammonia, or 2) the conversion into the corresponding phsphoric dichloride in its primary hydroxyl group subsequent reaction with protected L-serine or inositol and deprotection to give a compound of the formula (XIV):

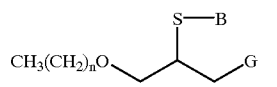  (XIV)

wherein n is an integer of 13 to 17 and G is a group selected from the group consisting of:

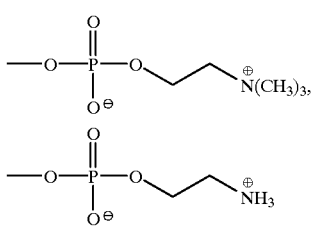

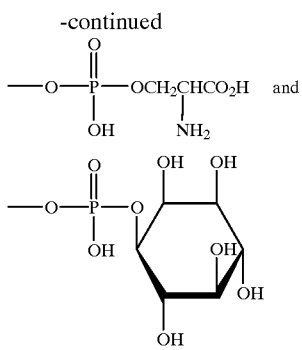

and B is as defined above.

The compound (XIV) is subjected to deprotection under mild conditions so as to liberate a thiol group while avoiding destruction of phsphoric ester moiety to give a compound of the formula (XIV'):

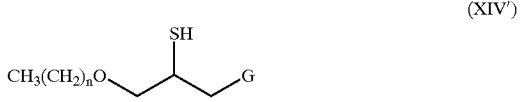
(XIV')

wherein G is as defined above. The thiol (XIV') is subjected to the condensation with a compound of the formula A—OH (wherein A is $C_{14}$–$C_{20}$ acyl group) to give a compound of the formula (I):

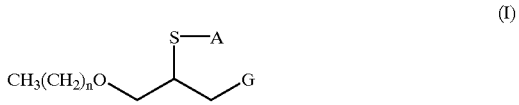
(I)

wherein n, A and G are as defined above.

Each process will be described in more detail below.

(1) Preparation of Compound (IV), Step (1)

The coupling reaction between 1,2-O-isopropylideneglycerol (II) and Compound (III) to form an ether bond is carried out under anhydrous conditions in the presence of a base such as sodium hydride, potassium hydride, n-butyllithium, lithium diisopropylamide, potassium tert-butoxide or the like in a solvent such as tetrahydrofuran, dimethylformamide, dimethyl sulfoxide, benzene, 1,2-dimethoxyethane or the like at a temperature of −20 to 100° C., preferably 0 to 80° C. Generally, the compound of the formula (III) can form an ether with an alcohol and the typical examples thereof include halides (Y=halogen), alkylsulfonyloxy, arylsulfonyloxy (Y=$OSO_2CH_3$, $OSO_2C_6H_5$, $OSO_2C_6H_4CH_3$, $OSO_2CF_3$).

(2) Preparation of Compound (V), Step (2)

The deprotection reaction of the acetonide where the diol (V) is prepared from Compound (IV) is carried out at a temperature of 0 to 100° C. in the presence of an acid such as hydrochloric acid, sulfuric acid, acetic acid, or trifluoroacetic acid in a solvent such as methanol, ethanol, dioxane, tetrahydrofuran, 1,2-dimethoxyethane, water, or a mixture thereof.

(3) Preparation of Compound (VII), Step (3)

Compound (V) is reacted with a reagent of the formula $R^1$—$X^1$ (VI) (e.g., trityl halide, acetyl halide, methoxymethyl halide, benzoyl halide, t-butyldimethylsilyl halide) which is generally used for protecting hydroxyl group in the presence of a base (e.g., triethylamine, pyridine, diisopropylethylamine, sodium hydride, imidazole) or in the presence of 3,4-dihydro-2H-pyran and pyridinium p-toluenesulfonate in a solvent such as dichloromethane, tetrahydrofuran, dimethylformamide or a mixture thereof at a temperature from 0 to 100° C.

(4) Preparation of Compound (IX), Step (4)

Compound (VII) is reacted with a sulfonylating agent of the formula $R^2$—$SO_2X^2$ (VIII) (e.g., methanesulfonyl chloride, phenylsulfonyl chloride, p-toluenesulfonyl chloride) at about −20 to 20° C. in the presence of a base (e.g., triethylamine, pyridine) in a solvent (e.g., dichloromethane, tetrahydrofuran).

(5) Preparation of Compound (XI), Step (5)

Compound (IX) is reacted with a thiocarboxylic acid metal salt of the formula $R^3S$—M (X) (wherein $R^3$ is alkanoyl or arylcarbonyl and M is an alkali metal) such as potassium thioacetate at about 50 to 100° C. in an appropriate solvent (e.g., dimethylformamide).

(6) Preparation of Compound (XII), Step (6)

Compound (XI) is subjected to solvolysis to give Compound (XII).

Compound (XI) is treated with an alkali such as sodium hydroxide, potassium hydroxide or sodium methoxide in an appropriate solvent (e.g., methanol, ethanol, tetrahydrofuran, water or a mixture thereof) to remove $R^3$. Alternatively, $R^3$ can be removed by treating the compound (XI) with a metal hydride such as $LiBH_4$, $LiAlH_4$ or the like in a solvent such as tetrahydrofuran, 1,2-dimethoxyethane, diethyl ether or the like.

(7) Preparation of Compound (XIII), Step (7)

"B" is a group which can be deprotected under a mild condition which does not affect the phosphoric ester moiety, example of which includes trityl, p-nitrobenzyl, diphenylmethyl and acyl as shown below. The compound (XIII) can be in the form of disulfide.

The protection of thiol group and removal of $R^1$ of Compound (XII) can be carried out as follows:

(i) Compound (XII) is converted into the S-trityl form by reacting with triphenylchloromethane at −20 to 20° C. in the presence of a base (e.g., triethylamine) in an appropriate solvent (e.g., tetrahydrofuran, acetonitrile) followed by removal of $R^1$ under a suitable condition. For example, the trityl compound is treated with sodium hydroxide in methanol/water or with hydrochloric acid in tetrahydrofuran.

(ii) Compound (XII) is reacted with p-nitrobenzyl chloride at 0 to 20° C. in the presence of a base (e.g., sodium hydride) in an appropriate solvent (e.g., toluene) to give a compound in the form of S-p-nitrobenzyl which is in turn subjected to the removal of $R^1$ in the same manner as mentioned above.

(iii) Compound (XII) is treated with benzhydrol in the presence of trifluoroacetic acid to give a compound of S-diphenylmethyl form which is in turn subjected to the removal of $R^1$ in the same manner as mentioned above;

(iv) Compound (XII) is reacted with a $C_1$–$C_8$ acyl chloride in the presence of a base (e.g., pyridine) in an appropriate solvent (e.g., dichloromethane) to give a compound of S-acyl form which is in turn subjected to the removal of $R^1$ in the same manner as mentioned above; or (v) After removal of $R^1$ in the same manner as mentioned above, the compound (XII) is treated with an oxidizing agent (e.g., bromine) in the presence of a base (e.g., aqueous potassium hydrogencarbonate solution) in an appropriate solvent (e.g., dichloromethane), to give a compound of the formula (XIII) in the form of self-dimer (disulfide).

The protection of the thiol group is also carried out after removing $R^1$ of the compound (XII), which results in the compound (XIII).

When $R^1$ is trityl group, it can be transferred from oxygen to sulfur atom by treating the compound (XII) with an acid (e.g., boron trifluoride-diethyl ether complex) at −30 to 0° C. in an appropriate solvent (e.g., dichloromethane) to give the corresponding compound (XIII) in one step. Therefore, the trityl group as $R^1$ is suitable as hydroxy-protecting group.

(8) Preparation of Compound (XIV), Step (8)

Compound (XIII) is reacted with 2-chloro-2-oxo-1,3,2-dioxaphospholane in the presence of a base (e.g., triethylamine) in an appropriate solvent (e.g., benzene) to form a cyclic phosphoric ester which is then treated with an amine (e.g., trimethylamine) or ammonia. Alternatively, the compound (XIII) is reacted with phosphorus oxychloride in the presence of a base (e.g., triethylamine) in an appropriate solvent (e.g., chloroform) to give a compound in the form of phosphoric dichloride, which is then reacted with the protected L-serine (e.g., N-t-butoxycarbonyl-L-serine t-butyl ester) or protected inositol (e.g., 2,3:5,6-di-O-isopropylidene-4-O-(4-methoxy-2H-tetrahydro-4-pyranyl)-myo-inositol). The protecting group on L-serine or inositol can be removed under mild acidic conditions.

(9) Preparation of Compound (I), Step (9)

The deprotection of the compound (XIV) is carried out using any of conventional methods which are mild and effective to remove "B" while avoiding destruction of the phosphoric diester moiety. For example, when B is trityl group, the deprotection can be done through the treatment with silver nitrate followed by treatment with hydrogen sulfide or hydrogen chloride; when B is p-nitrobenzyl group, through the hydrogenation; when B is diphenylmethyl group, through the treatment with trifluoroacetic acid/anisole; when B is acyl group, through the treatment with dilute alkali or the reduction with lithium borohydride or the like; or when the compound (XIII) is disulfide, through the treatment with tri-n-butylphosphine/water. The resultant thiol is reacted with a compound of the formula A—OH (wherein A is $C_{14}$–$C_{20}$ acyl group), for example, cis-8,11,14-eicosatrienoic acid, arachidonic acid, cis-5,8,11,14,17-eicosapentaenoic acid or the like, at a temperature of 0° C. to room temperature in the presence of a condensing agent (e.g., dicyclohexylcarbodiimide, 1,1'-carbonyldiimidazole, 1-(3-dimethylaminopropyl)-3-ethylcarbodiimide) in a solvent (e.g., dichloromethane) to form thioester bond.

The starting material and intermediates described above may be their optically active isomers and the method of the present invention can be put into practice using any isomers or racemates thereofs.

The present method comprises one or more of the above-mentioned processes each falling within the scope of the present invention. Specifically, the present invention relates to a method comprising one or more of these processes, e.g., process (9); process (8); process (7); processes (4), (5) and (6); or processes (1)–(9).

The outstanding features of the present invention can be summarized as follows:

(1) The method of the present invention comprises one or more process(es) each being able to be conducted with simple and safe operations and is applicable to a mass production in respect to yield and manipulation.

(2) A compound of the formula (XII) wherein $R^1$ is a trityl group can be stored stably and is a preferable intermediate because the thiol group resists being oxidized into disulfide thereby preventing the formation of dimer. In another aspect, by means of trityl-transfer reaction, the trityl group can be converted into thiol-protecting group, which improves the efficiency.

(3) The final process where the compound (XIV) is converted into compound (I) proceeds so smoothly that it is possible to obtain the compound (I) of extremely high chemical purity.

As can be seen from the above, the method of the present invention is especially suited for producing a compound of the formula (I) wherein a labile aliphatic carboxylic acid such as cis-8,11,14-eicosatrienoic acid, arachidonic acid or cis-5,8,11,14,17-eicosapentaenoic acid is bound in sn-2 position via a thioester bond, which compound cannot be obtained efficiently by conventional methods.

The compounds (XI), (XII), (XIII), (XIV) and those derived therefrom by deprotection are novel and have hitherto been unpublished.

The present invention also provides each of these compounds useful as an intermediate in the preparation of not only the compound (I) of the present invention but also any organic compounds and the method of producing the same.

The compound (XIV), a very important intermediate, is in the stable crystalline form and therefore can be kept for a long term safely.

The following Examples are provided to further illustrate the present invention and are not to be construed as limiting the scope thereof.

EXAMPLE 1

Preparation of Compound IV-1 (3-O-hexadecyl-1,2-O-isopropylidene-sn-glycerol)

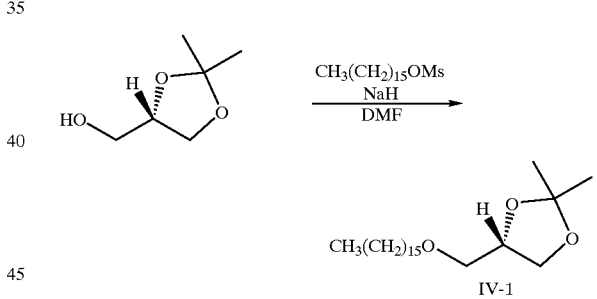

Sodium hydride (60% in oil) (7.26 g, 0.151 mole×1.2) is placed in a three-necked flask (2 L). After washing with n-hexane (25 ml×4) to remove the adhering oil, anhydrous dimethylformamide (300 ml) is added to obtain a suspension. To the suspension is added under nitrogen atmosphere and ice-cooling a solution of D-1,2-O-isopropylidene-sn-glycerol (20.0 g, 0.151 mole) in anhydrous dimethylformamide (300 ml) and the mixture is stirred vigorously with mechanical stirrer for 30 min. To the reaction mixture is added under ice-cooling a solution of hexadecyl methanesulfonate (58.21 g, 0.151 mole×1.2) in anhydrous dimethylformamide (300 ml) and the mixture is stirred for 17 hr at room temperature. The reaction mixture is poured into ice-cold water (2.5 L) and extracted with ethyl acetate. The extract is washed with water and saturated brine successively, dried over sodium sulfate and concentrated. The residue is purified by column chromatography on silica gel eluting with n-hexane/ethyl acetate (from 98:2 to 95:5) to give the compound IV-1 (52.37 g; yield 97%) as a colorless oil.

Elementary analysis($C_{22}H_{44}O_3$); Calcd: C, 74.10; H, 12.40; Found: C, 73.97; H, 12.39. $[\alpha]_D^{22}$+8.2±0.2 (c 2.12, $CHCl_3$); MS m/z: 356 (M+); IR ($CHCl_3$): 1465, 1381, 1372, 1236, 1133, 1114 cm$^{-1}$. $^1$H NMR ($CDCl_3$) δ: 0.88(t,J=6.4 Hz,3H), 1.10–1.40(m,26H), 1.36(s,3H), 1.42(s,3H), 1.45–1.65(m,2H), 3.36–3.58(m,4H), 3.73(dd,J=8.2,6.4 Hz,1H), 4.06(dd,J=8.2,6.4 Hz,1H), 4.27(tt,J=6.1,6.1 Hz,1H).

EXAMPLE 2

Preparation of Compound V-1 (3-O-hexadecyl-sn-glycerol)

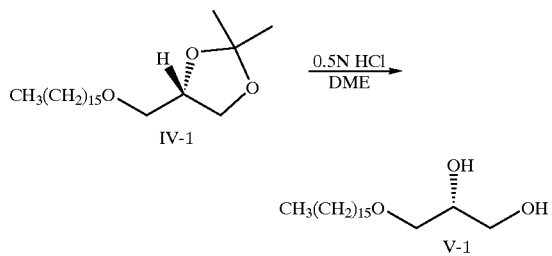

To a solution of compound IV-1 (52.37 g, 0.147 mole) in 1,2-dimethoxyethane (370 ml) is added 0.5 N HCl (147 ml) at room temperature and the mixture is heated to reflux for 1.5 hr. The reaction mixture is cooled, concentrated and the residue is diluted with ethyl acetate (1.5 L). The solution is washed with water (350 ml), saturated aqueous sodium hydrogencarbonate solution (100 ml) and saturated brine (200 ml) successively, dried over sodium sulfate and concentrated. The resultant crude crystals are washed with n-hexane to give the compound V-1 (45.30 g; yield 97%) as colorless crystals.

M.p. 66–66.5° C. Elementary analysis ($C_{19}H_{40}O_3$); Calcd: C, 72.10; H, 12.74; Found: C, 71.95; H, 12.68. $[\alpha]_D^{24.5}$–2.7±0.4° (c 1.005, $CHCl_3$); MS m/z: 317 (MH+); IR (KBr): 3415, 3335, 3250, 1460, 1130, 1050 cm$^{-1}$. $^1$H NMR ($CDCl_3$) δ: 0.88(t,J=6.4H,3H), 1.10–1.45(m,26H), 1.45–1.65(m,2H), 2.20(dd,J=6.4,5.4H,OH), 2.63(d,J=5.0 Hz,OH), 3.40–3.93(m,7H).

EXAMPLE 3

Preparation of Compound XI-1 (2-S-acetyl-1-O-hexadecyl-3-O-trityl-sn-2-thioglycerol)

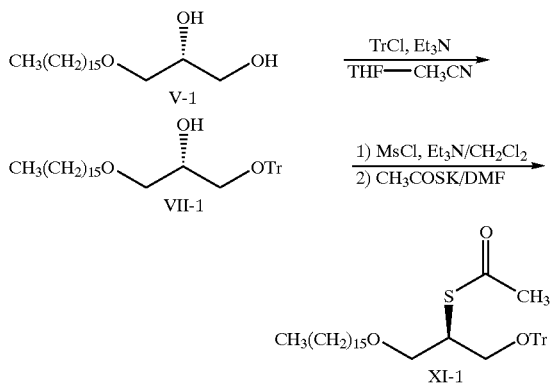

A solution of compound V-1 (42.98 g, 0.136 mole), triphenylmethyl chloride (45.43 g, 0.136 mole×1.2) and triethylamine (37.9 ml, 0.136 mole×1.2) in anhydrous tetrahydrofuran (470 ml)/anhydrous acetonitrile (120 ml) is heated to reflux for 15 hr under nitrogen atmosphere. The reaction mixture is concentrated and filtrated to remove the precipitated triethylamine hydrochloride. The salt is washed thoroughly with ethyl acetate (700 ml). The filtrate and the washings are combined and washed with water (200 ml), 0.15 N HCl (230 ml), saturated aqueous sodium hydrogencarbonate solution (150 ml) and saturated brine (200 ml) successively. The solution is dried over sodium sulfate and concentrated to obtain the compound VII-1 (3-O-hexadecyl-1-O-trityl-sn-glycerol) (85.36 g) as pale-yellowish crude crystals.

The resultant compound VII-1 (85.36 g) is dissolved in anhydrous methylene chloride (880 ml). To the solution are added gradually and successively triethylamine (31.9 ml, 0.229 mole) and methanesulfonyl chloride (11.8 ml, 0.152 mole) at –5° C. under nitrogen atmosphere. After stirring for another 1.5 hr at the same temperature, the reaction mixture is poured into ice-cold water (500 ml). The organic phase is separated and the aqueous phase is extracted with methylene chloride (100 ml). The organic phases are combined and washed with 0.3 N HCl (280 ml), saturated aqueous sodium hydrogencarbonate solution (100 ml) and saturated brine (200 ml) successively. The solution is dried and concentrated to give a mesylate (94.07 g) as a pale-yellow oil.

The mesylate (94.07 g) is dissolved in anhydrous dimethylformamide (800 ml). To the solution is added potassium thioacetate (33.74 g, 0.295 mole) and the mixture is stirred for 16 hr under nitrogen atmosphere while heating on an oil bath (90° C.), when potassium thioacetate (16.87 g, 0.148 mole) is added and the reaction mixture is stirred under the same conditions for another 4 hr. After cooling, the reaction mixture is poured into ice-cold water (2.4 L) and extracted with ethyl acetate (1 L×3). The extract is washed with water (800 ml×3) and saturated brine (800 ml) successively, dried and concentrated. The residue is purified by column chromatography on silica gel eluting with n-hexane/toluene (from 5:1 to 1:2) to give the compound XI-1 (68.75 g; yield from compound V-1, 82%) as a reddish-brown oil.

MS m/z: 617 (MH+); IR ($CHCl_3$): 1686,1490,1466,1448, 1133,1114 cm$^{-1}$. $^1$H NMR ($CDCl_3$) δ: 0.88(t,J=6.4 Hz,3H), 1.10–1.40(m,26H), 1.40–1.60(m,2H), 2.31(s,3H), 3.22(dd, J=9.2,5.6 Hz,1H), 3.37(t,J=6.6 Hz,2H), 3.39(dd,J=9.2,3.8 Hz,1H), 3.65(d,J=6.0 Hz,2H), 3.80–3.97(m,1H), 7.15–7.50 (m,15H).

EXAMPLE 4

Preparation of Compound XII-1 (1-O-hexadecyl-3-O-trityl-sn-2-thioglycerol)

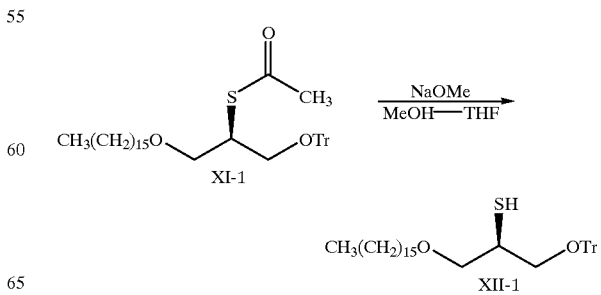

To a solution of compound XI-1 (68.75 g, 0.111 mole) in anhydrous methanol (400 ml)/anhydrous tetrahydrofuran (200 ml) is added under ice-cooling gradually a solution of 28 wt. % sodium methoxide in methanol (23.6 ml, 0.111 mole×1.1). The reaction mixture is stirred for 30 min at the same temperature under nitrogen atmosphere and concentrated. The residue is diluted with ethyl acetate (700 ml). The solution is washed with 0.4 N hydrochloric acid (320 ml), saturated aqueous sodium hydrogencarbonate solution (100 ml) and saturated brine (150 ml) successively, dried and concentrated. The residue is purified by column chromatography on silica gel eluting with n-hexane/toluene (3:1) to give the compound XII-1 (60.68 g; yield 95%) as colorless crystals.

M.p. 61.5–63.0° C. Elementary analysis($C_{38}H_{54}O_2S$) Calcd: C, 79.39; H, 9.47, S, 5.58 Found: C, 79.28; H. 9.46, S, 5.55 $[\alpha]_D^{25}$+3.5±0.4° (c 1.008, $CHCl_3$) LSIMS m/z: 597 ([M+Na]$^+$) IR (KBr): 3430, 1490, 1468,. 1450, 1443, 1118, 1093 cm$^{-1}$. $^1$H NMR ($CDCl_3$) δ: 0.88(t,J=6.4 Hz,3H), 1.10–1.40(m,26H), 1.40–1.65(m,2H), 1.89(d,J=8.2 Hz,SH), 2.95–3.15(m,1H), 3.26(dd,J=9.2,5.8 Hz,1H), 3.32(dd,J=9.2, 5.4 Hz,1H), 3.40(t,J=6.6 Hz,2H), 3.55–3.70(m,2H), 7.15–7.50(m,15H).

EXAMPLE 5

Preparation of Compound XIII-1 (1-O-hexadecyl-2-S-trityl-sn-2-thioglycerol)

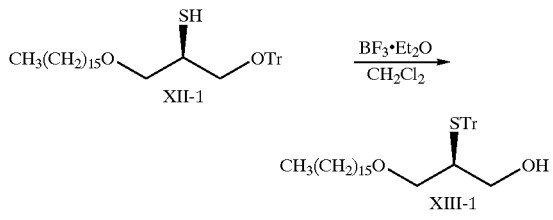

To a solution of compound XII-1 (60.68 g, 0.106 mole) in anhydrous methylene chloride (1.2 L) is added gradually boron trifluoride-diethyl ether complex (14.3 ml, 0.106 mole×1.1) at −10° C. under nitrogen atmosphere. After stirring for another 45 min under the same conditions, the reaction mixture is poured into ice-cold saturated aqueous sodium hydrogencarbonate solution (200 ml) and extracted with methylene chloride. The extract is washed with saturated brine (200 ml), dried and concentrated. The residue is purified by column chromatography on silica gel [eluent: n-hexane/toluene (1:1)–ethyl acetate] to give the compound XIII-1 (51.86 g; yield 85%) as a colorless oil.

Elementary analysis($C_{38}H_{54}O_2S$) Calcd: C, 79.39; H, 9.47; S, 5.58 Found: C, 79.23; H, 9.51; S, 5.52. $[\alpha]_D^{23}$−25.8±0.3° (c 2.28, $CHCl_3$) LSIMS m/z: 597 ([M+Na]$^+$) IR ($CHCl_3$): 3574, 3468, 1595, 1488, 1465, 1444, 1133, 1110 cm$^{-1}$. $^1$H NMR ($CDCl_3$) δ: 0.88(t,J=6.4 Hz,3H), 1.10–1.35 (m,26H), 1.35–1.55(m,2H), 2.54–2.72(m,2H), 3.00–3.58(m, 6H), 7.15–7.35(m,9H), 7.40–7.50(m,6H).

EXAMPLE 6

Preparation of Compound XIV (1-O-hexadecyl-2-S-trityl-sn-2-thioglycero(3)phosphocholine)

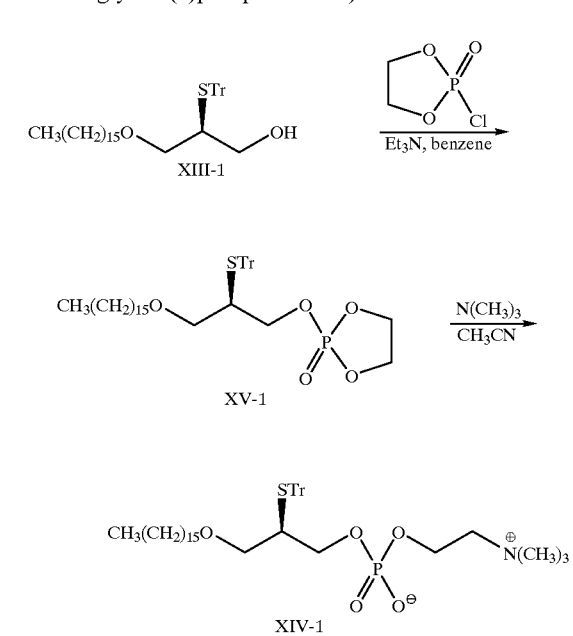

To a solution of compound XIII-1 (39.83 g, 69.3 mmole) and triethylamine (22.0 ml, 69.3 mmole×2.3) in anhydrous benzene (950 ml) is added a solution of 2-chloro-2-oxo-1,3,2-dioxaphospholane (18.74 g, 69.3 mmole×1.9) in anhydrous benzene (100 ml) at room temperature under nitrogen atmosphere. After stirring for another 3.5 hr under the same conditions, the reaction mixture is filtered to remove the precipitated salts. The salts are washed with a small amount of anhydrous benzene. The filtrate and washings are combined and concentrated to give the compound (XV-1) (1-O-hexadecyl-2-S-trityl-3-O-(2-oxo-1,3,2-dioxaphospholan-2-yl)-sn-2-thioglycerol) as a pale-brown oil.

A solution of the resultant compound (XV-1) in 3.81 M trimethy,lamine/acetonitrile solution (96 ml, 69.3 mmole× 5.3) is placed in a tube, which is then sealed and heated on an oil bath (50° C.) for 16 hr. The reaction solution is concentrated and the residue is diluted with methyl ethyl ketone (1.5 L). The solution is washed with water (150 ml×3) and saturated brine (100 ml×2) successively. After removing the solvent in vacuo, the residue is purified by column chromatography on silica gel eluting with chloroform/methanol/water (32:9:1) to give the compound XIV-1 (35.95 g; yield 70%) as colorless crystals.

M.p. 127–136° C. Elementary analysis ($C_{43}H_{66}O_5NPS.H_2O$) Calcd: C, 68.13; H. 9.04; N, 1.85; P, 4.09; S, 4.23 Found: C, 68.06; H, 8.97; N, 2.03; P, 4.35; S, 4.31 $[\alpha]_D^{25}$+29.9±0.4° (c 2.003, $CHCl_3$) LSIMS m/z: 740 (MH$^+$) IR (KBr): 3393, 1488, 1468, 1445, 1257, 1091, 1064, 1004, 968 cm$^{-1}$. $^1$H NMR ($CD_3OD$) δ: 0.89(t,J=6.4 Hz,3H), 1.10–1.50(m,28H), 2.50–2.65(m,1H), 2.84(dd,J=10.2,4.4 Hz,1H), 3.05–3.27(m,3H), 3.18(s,9H), 3.50–3.65(m,2H), 3.75–3.95(m,2H), 4.10–4.30(m,2H), 7.15–7.40(m,9H), 7.45–7.55(m,6H).

EXAMPLE 7

Preparation of Compound I-1 (2-S-arachidonoyl-1-O-hexadecyl-sn-thioglycero(3)phosphocholine)

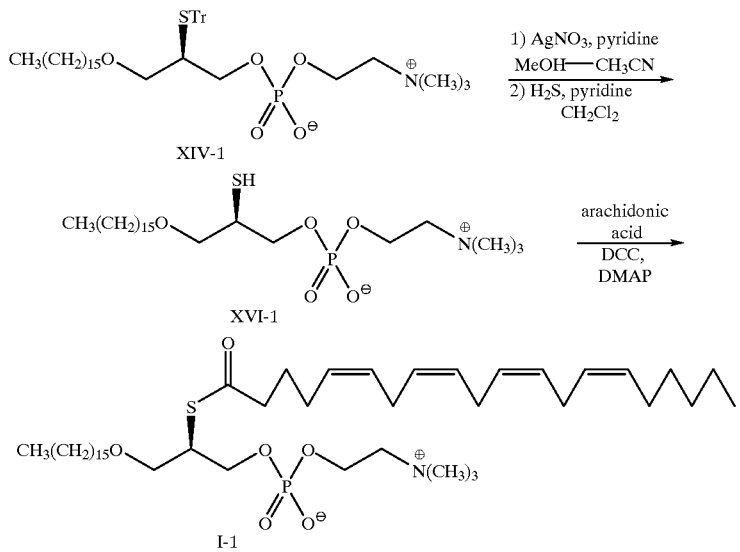

Compound XIV-1 (20.0 g, 26.4 mmole) is dissolved in methanol (20 ml)/acetonitrile (200 ml) and pyridine (4.69 ml, 26.4 mmole×2.2) is added thereto at room temperature. A solution of silver nitrate (8.96 g, 26.4 mmole×2.0) in acetonitrile (30 ml) is gradually added under ice-cooling and the mixture is stirred for another 30 min under ice-cooling. After the addition of ether (250 ml), the precipitated solid us collected by filtration. The solid is washed with acetonitrile/ether (1:1) (100 ml×3) and ether (100 ml) successively and dried to obtain the silver salt (17.3g).

To a suspension of the silver salt (17.3 g) in methylene chloride (380 ml) is added pyridine (4.27 ml, 26.4 mmole× 2.0), and hydrogen sulfide gas (15 ml/min) is bubbled through the suspension for 30 min while vigorously stirring under ice-cooling. After stopping the introduction of hydrogen sulfide gas, the resulting solution is stirred for another 1 hr at room temperature whereby a solution of the compound XVI-1 ( 1-O-hexadecyl-sn-2-thioglycero(3) phosphocholine) in methylene chloride is obtained.

After the reaction solution is concentrated to about ⅓ of its original volume, it is added to a solution of arachidonic acid (7.23 g, 26.4 mmole×0.9) and 4-dimethylaminopyridine (3.23 g, 26.4 mmole×1.0) in methylene chloride (150 ml) under ice-cooling. To the mixture is added a solution of dicyclohexylcarbodiimide (5.45 g, 26.4 mmole×1.0) in methylene chloride (15 ml). The reaction mixture is stirred for 1.5 hr at room temperature, when 4-dimethylaminopyridine (646 mg, 26.4 mmole×0.2) and dicyclohexylcarbodiimide (1.09 g, 26.4 mmole×0.2) are added thereto. The mixture is stirred for another 1.5 hr at room temperature.

To the reaction solution is added methyl ethyl ketone (500 ml) and the mixture is stirred for 5 min under ice-cooling. The reaction mixture is filtered to remove urea which in turn is washed with methyl ethyl ketone (100 ml). To the filtrate is added 3% citric acid (360 ml) and the mixture is stirred for 15 min under ice-cooling. The resultant black precipitates are filtered off using powdered filter paper and washed thoroughly with methyl ethyl ketone (470 ml). The filtrate and washings are combined. The organic phase is separated and washed with 3% citric acid (200 ml) and water (200 ml) successively. Each aqueous phase is washed with methyl ethyl ketone (500 ml×2). All the organic phases are combined, dried over sodium sulfate and concentrated. The residue is purified by flash column chromatography on silica gel [eluent: chloroform→chloroform/methanol/water (64:9:1)→chloroform/methanol/water (32:9:1)] to give the compound I-1 (15.8 g; yield 76%) as a colorless oil. As the compound I-1 is very unstable at room temperature, it is immediately dissolved in freshly distilled chloroform (containing 1% ethanol) (700 ml), sealed with argon and stored in a freezer at −80° C.

HR-LSIMS (as $C_{44}H_{83}NO_6SP$); Calcd: 784.5674 Found: 784.5673 IR ($CHCl_3$): 3399, 1682, 1603, 1467, 1240, 1087cm$^{-1}$. $^1H$ NMR ($CDCl_3$) δ: 0.88(t,J=6.4 Hz,3H), 0.89 (t,J=6.4 Hz,3H), 1.20–1.42(m,32H), 1.42–1.60(m,2H), 1.60–1.80(m,2H), 1.96–2.18(m,4H), 2.54(t,J=7.6 Hz,2H), 2.72–2.92(m,6H), 3.30–3.47(m,2H), 3.40(s,9H), 3.48–3.68 (m,2H), 3.75–4.03(m,5H), 4.26–4.42(m,2H), 5.24–5.50(m, 8H). $^{13}C$ NMR ($CDCl_3$) δ: 14.11, 14.14, 22.60, 22.72, 25.45, 25.64, 26.11, 26.42, 27.24, 29.35, 29.40, 29.59, 29.69, 29.75, 31.54, 31.96, 43.63, 44.10, 44.20, 54.39, 59.25, 59.30, 64.15, 64.21, 66.35, 66.41, 69.16, 71.46, 127.52, 127.80, 128.05, 128.32, 128.62, 128.65, 129.09, 130.50, 198.96. Thin-layer chromatography (TLC): Rf value=0.41.

Conditions:
 Merck Silica gel 60F-254 pre-coated plate; and
 Developing solvent: chloroform/methanol/water (65:25:4)

High performance liquid chromatography (HPLC):
 Retention time=4.45 minute.
 Conditions:
  Column: Finepak SIL (Jasco, 5 μm, 4.6φ×150 mm);
  Mobile phase: acetonitrile/water (4:1);
  Flow rate: 0.8 ml/min; and
  Detection: UV spectrum at 225 nm.

What we claim is:

1. A compound of the formula (XIII):

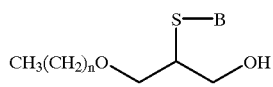

wherein n is an integer of 13 to 17 and B is an S-protecting group selected from the group consisting of t-butoxycarbonyl, benzyloxycarbonyl, benzyl, 4-methoxybenzyl, 3,4-dimethoxybenzyl, 4-nitrobenzyl, diphenylmethyl and trityl.

2. A method of producing a compound of the formula (XIII):

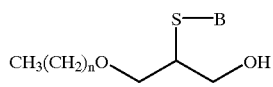

wherein n is an integer of 13 to 17 and B is an S-protecting group selected from the group consisting of t-butoxycarbonyl, benzyloxycarbonyl, benzyl, 4-methoxybenzyl, 3,4-dimethoxybenzyl, 4-nitrobenzyl, diphenylmethyl and trityl, which comprises protecting the thiol group of a compound of the formula (XII):

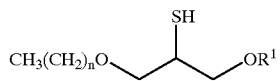

wherein n is as defined above and $R^1$ is a hydroxy-protecting group in the presence of a base and removing $R^1$ under deprotection conditions.

3. A method of producing a compound of the formula (XIII):

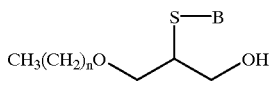

wherein n is an integer of 13 to 17 and B is trityl, which comprises treating a compound of the formula (XII):

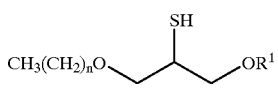

wherein n is as defined above and $R^1$ is trityl, with an acid to transfer the said trityl group from hydroxyl group to thiol group in one step.

4. A compound of the formula (XII):

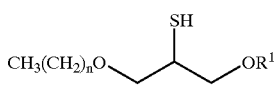

wherein n is an integer of 13 to 17 and $R^1$ is trityl.

* * * * *

UNITED STATES PATENT AND TRADEMARK OFFICE
CERTIFICATE OF CORRECTION

PATENT NO. : 5,981,778
DATED : November 9, 1999
INVENTOR(S) : Mitsuaki OHTANI et al.

It is certified that error appears in the above-identified patent and that said Letters Patent is hereby corrected as shown below:

Title page, item

[30]   Foreign Application Priority Data should read --
    September 20, 1994    [JP]    Japan    224679/1994

Signed and Sealed this

Thirtieth Day of May, 2000

Attest:

Q. TODD DICKINSON

Attesting Officer         Director of Patents and Trademarks